United States Patent
Pedersen

(10) Patent No.: US 8,871,195 B2
(45) Date of Patent: Oct. 28, 2014

(54) **BACTERIA *THYA*(−) MUTANTS WITH INCREASED VITAMIN K**

(71) Applicant: Chr. Hansen A/S, Hoersholm (DK)

(72) Inventor: Martin Pedersen, Copenhagen S. (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 13/781,455

(22) Filed: Feb. 28, 2013

(65) Prior Publication Data

US 2013/0243742 A1  Sep. 19, 2013

Related U.S. Application Data

(63) Continuation of application No. 13/375,449, filed as application No. PCT/EP2010/057629 on Jun. 1, 2010, now abandoned.

(30) Foreign Application Priority Data

Jun. 3, 2009  (EP) .................................. 09161782

(51) Int. Cl.
*A01N 63/00* (2006.01)
*A23C 9/12* (2006.01)
*A23L 1/30* (2006.01)

(52) U.S. Cl.
USPC .......... 424/93.45; 424/93.46; 426/43; 426/72

(58) Field of Classification Search
None
See application file for complete search history.

(56) References Cited

U.S. PATENT DOCUMENTS

| 7,718,407 B2 * | 5/2010 | Benedetti et al. ............ 435/133 |
| 7,780,961 B2 * | 8/2010 | Steidler ........................ 424/93.2 |
| 2009/0238774 A1 * | 9/2009 | Connolly et al. .............. 424/48 |

FOREIGN PATENT DOCUMENTS

| WO | WO-00/01799 | 1/2000 |
| WO | WO-2008/040784 A1 | 4/2008 |
| WO | WO-2008/040793 A1 | 4/2008 |

OTHER PUBLICATIONS

Alexander Bolotin et al., "The Complete Genome Sequence of the Lactic Acid Bacterium *Lactococcus lactis* ssp. lactis IL1403", Genome Research, 11: 731-753, 2001.
Database WPI Week 200030 Thomson Scientific, London, GB, AN 2000-342455, XP002556520 & JP 2000-080043 A (SUMI H) Mar. 21, 2000, Abstract.
Database WPI Week 200148, Thomson Scientific, London, GB, AN 2001-445891, XP002556519 & JP 2001 136959 A (Honda Trading KK) May 22, 2001, Abstract.
International Search Report PCT/EP2010/057629 dated Jul. 8, 2010.
Takashi Morishita et al., "Production of Menaquinones by Lactic Acid Bacteria", J. Dairy Sci. 82:1897-1903, 1999.
Yoshinori Tsukamoto et al., "Construction of a *Bacillus subtilis* (natto) with High Productivity of Vitamin K2 (Menaquinone-7) by Analog Resistance", Bioscience Biotechnology Biochemistry, Japan Society for Bioscience, Biotechnology, and Agrochemistry, Tokyo, Japan, vol. 65, No. 9, Jan. 1, 2001, pp. 2007-2015.

* cited by examiner

*Primary Examiner* — Christopher R Tate
*Assistant Examiner* — Douglas F White
(74) *Attorney, Agent, or Firm* — Foley & Lardner LLP

(57) ABSTRACT

Bacteria thyA(−) mutants with increased vitamin K and use of these thyA(−) mutants for making a composition/product for treatment and/or prevention of vitamin K deficiency in a mammal (e.g. a human).

14 Claims, 1 Drawing Sheet

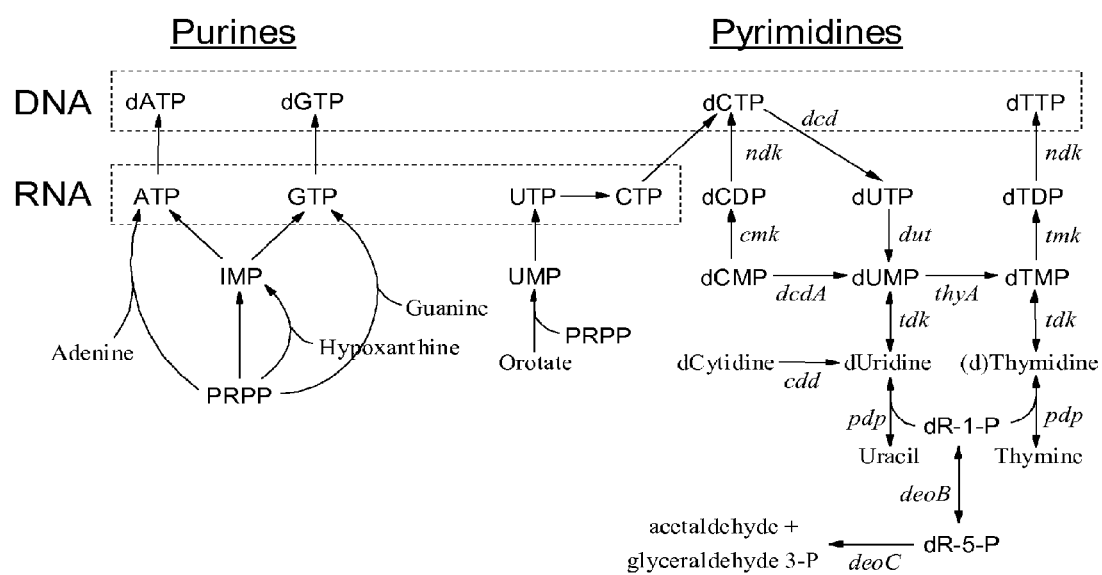

ional patent application No. 09161782.9, filed on Jun. 3, 2009. The content of each of these prior applications is incorporated herein by reference.

BACTERIA THYA(-) MUTANTS WITH INCREASED VITAMIN K

CROSS REFERENCE TO RELATED APPLICATIONS

This application is a continuation of U.S. patent application Ser. No. 13/375,449, filed on Nov. 30, 2011, which is the U.S. national phase of PCT/EP2010/057629, filed on Jun. 1, 2010, which claims priority from European patent application No. 09161782.9, filed on Jun. 3, 2009. The content of each of these prior applications is incorporated herein by reference.

FIELD OF THE INVENTION

The present invention relates to bacteria thyA(-) mutants with increased vitamin K and use of these thyA(-) mutants for making a composition/product for treatment and/or prevention of vitamin K deficiency in a mammal (e.g. a human).

BACKGROUND ART

As known, lactic acid bacteria (LAB) are intensively used in the dairy industry for making different animal milk fermented products such as e.g. yogurt, cheese etc.

Vitamin K is important for a number of human/animal health issues such as bone health.

The lactic acid bacteria *Lactococcus lactis* and *Leuconostoc lactis* are natural producers of vitamin K2 [menaquinones] (Morishita T et al. 1999. Production of Menaquinones by Lactic Acid Bacteria. J. Dairy. Sci. 82:1897-1903).

The vitamin K2 is constituents of the bacterial plasma membrane—i.e. vitamin K2 is present in the membrane of the LAB.

Generally speaking, the amount of vitamin K2 produced by wild-type lactic acid bacteria is not sufficiently high to make a commercially relevant product comprising vitamin K2—e.g. a dairy product with a sufficiently high amount of vitamin K2.

Accordingly, work has been done to identify mutants of *Lactococcus lactis* capable of producing an increased amount of vitamin K2—see e.g. WO2008/040793A1 (Danone).

Further, in WO2008/040784A1 (Danone) it is described that an increased amount of produced vitamin K2 can be obtained by fermenting milk with LAB under conditions, where the LAB are not in the growth phase but in what is termed "resting cells" phase in WO2008/040784A1 (see e.g. claim 1).

Essentially, this is obtained by adding a relatively large amount of LAB to the milk.

As known in the art, when a relatively high amount of LAB is added to the milk there will virtually be no growth (cell division) of the LAB, due to the fact that the initially added large amount of LAB will rapidly produce so much lactic acid that the pH of the milk will drop to a pH e.g. below pH=4 and at this low pH there is no significant growth of the LAB.

Said in other words, when a large amount of LAB is added to milk the pH will drop so rapidly that the LAB do not have "time" for making growth (cell division).

As known to the skilled person the thyA gene is encoding thymidylate synthase. As shown in FIG. 1, when this thyA gene is inactivated in e.g. a LAB one gets a so-called thymidine auxotrophic mutant—i.e. a mutant strain that is not capable of cell division in a thymidine "limited" media due to it cannot synthesize dTTP without addition of thymidine and thereby cannot replicate their genome. As known, milk does not comprise a significant amount of thymidine and such thyA(-) mutant strain will therefore not have significant growth in milk.

WO00/01799A2 (Chr. Hansen A/S) describes the thyA(-) *Lactococcus lactis* mutant strain MBP71 deposited under the accession number DSM12891 and it is described that the thyA(-) strain is bacteriophage resistant.

It is not described or suggested that such a thyA(-) mutant strain could be used for making an increased amount of vitamin K2.

Further, in none of above and below cited prior art documents is it described or suggested that by inactivating the thyA gene in a LAB cell one could get increased vitamin K2 production.

For instance, the above discussed WO2008/040793A1 (Danone) mentions a number of genes that could be relevant for obtaining increased vitamin K2 production in LAB (see e.g. claim 5)—however none of these mentioned genes are the thyA gene or genes that in the present context may be said to be similar/related to the thyA gene.

JP 2001 136959 A (published May 2001) relates to a *Bacillus subtilis* microbial cell culture useful for preventing and treating osteoporosis, whereby said microbial cells are recovered before releasing vitamin K. The osteoporosis treating effect can be obtained by ingesting the microbial cell containing vitamin K, whereby said microbial cells can be incorporated in food or pharmaceutical product (cf. abstract).

JP 2000 080043 A (published March 2000) concerns oral pharmaceuticals/foodstuffs comprising a water soluble vitamin K fraction of *Bacillus natto* for the prevention of osteoporosis (cf. abstract).

The article (Tsukamoto et al; "Construction of a *Bacillus subtilis* (natto) with High Productivity of Vitamin K2 (Menaquinone-7) by Analog Resistance"; Bioscience Biotechnology Biochemistry; vol. 65(9), pages 2007-2015, 2001) reports on the construction of a *Bacillus subtilis* strain with high productivity of vitamin K2 (menaquinone-7/MK7). Hereby a strain OUV23481 with two-fold higher productivity of MK7 than that of a commercial strain is constructed as a mutant with analog resistance to 1-hydroxy-2-naphtoic acid (HNA), p-fluoro-D,L-phenylalanine (pFP), mfluoro-D,L-phenylalanine (mFP) and beta-2-thienylalanine (betaTA). Said mutant is classified as *Basillus subtilis* natto (cf. abstract, $2^{nd}$ paragraph of the right-hand column on page 2007 and $2^{nd}$ paragraph of left-hand column on page 2014).

SUMMARY OF THE INVENTION

The problem to be solved by the present invention is to provide a lactic acid bacteNunn capable of producing an increased amount of vitamin K2.

The solution is based on that the present inventors have identified that by inactivating the thyA gene in a LAB cell a thyA(-) mutant strain capable of producing an increased amount of vitamin K2 can be obtained.

In working examples herein this is clearly demonstrated for thyA(-) *Lactococcus lactis* mutant strain MBP71 deposited under the accession number DSM12891 (see WO00/01799A2 (Chr. Hansen A/S)—discussed above).

In Example 1 herein it is demonstrated that the thyA(-) mutant strain MBP71 produced about 3-fold higher amount of vitamin K2 as compared to the corresponding thyA(+) wild-type strain MBP68.

Further, in Example 1 both strains were added to the milk at inoculation level of OD=1.0. Such an inoculation level may be considered as adding a relatively large amount of LAB to the milk—i.e. as discussed above in both experiments a limited or no cell division of the LAB occurred—i.e. this means a condition termed "resting cells" in WO2008/040784A1 occurred (see discussion above).

Accordingly, the fact that the thyA(−) mutant strain MBP71 cannot replicate its genome in the milk can not be the only explanation for the SURPRISING result that the thyA(−) mutant strain produces significantly more vitamin K2.

Said in other words, the fact that thyA(−) mutant strains may be considered as "resting cells"—as discussed in WO2008/040784A1 (see above)—can NOT by itself explain the surprising result of significant increased vitamin K2 production.

In Example 2 herein it is demonstrated that it is not directly the starvation for dTTP that results in the increased vitamin K2, but rather the change in metabolism caused by the thyA gene in-activation.

In Example 3 herein a deletion mutant of purD was tested—such a mutant may be said to be another nucleotide metabolism related mutant (see e.g. FIG. 1 herein). The purD mutant did NOT work—i.e. it did not result in increased vitamin K2 production.

Overall, the results of Example 1 to 3 show that inactivation of the thyA gene had a surprising and unique positive effect on vitamin K2 production.

Such a thyA(−) mutant is therefore a useful means of supplying more vitamin K2 in for example dairy products, thereby e.g. improving bone health for the general population.

Further, since the working examples herein clearly demonstrate that the improvement (increased vitamin K2 production) is directly associated with the thyA gene as such there is objectively no reason for the skilled person to believe that the concept as described herein (i.e. making thyA(−) mutants) should not be generally applicable for making the herein relevant improved bacterial strains in general—i.e. not only improved *Lactococcus lactis* strains.

In the Morishita T et al. 1999 article discussed above it is described that different wild-type *Lactococcus* and *Leuconostoc* strains produce measurable amounts of vitamin K2 (see table 2 of the article).

Further, as known to the skilled person and as described on page 1899 of the Morishita T et al article—*Bacillus* are also potent producers of vitamin K.

In summary, in view of above it is evident that a bacterium from any of the genus *Lactococcus, Leuconostoc* or *Bacillus* would be a suitable candidate for making a thyA(−) mutant strain to thereby get a strain capable of making an increased amount of vitamin K2 as described herein.

Accordingly, a first aspect of the invention relates to a composition comprising bacteria containing vitamin K2, wherein the amount of bacteria present in the composition results in:
   (a): at least 0.10 μg/(rd or g) of vitamin K2 in the composition; and wherein
   (i): the bacteria are thyA(−) mutants; and
   (ii): the bacteria are bacteria selected from the group consisting of the genera:
   *Lactococcus, Leuconostoc* and *Bacillus;*
and wherein the composition is for use for treatment and/or prevention of vitamin K deficiency in a mammal.

A herein commercially relevant composition is e.g. a fermented milk food product (such as a dairy food product) such as a yogurt or a cheese.

Due to the high vitamin K content of such a dairy product as described herein and the use of it for treatment and/or prevention of vitamin K deficiency—such a dairy product may be termed a functional food product.

It is evident, that before being aware of the knowledge as described herein (i.e. high vitamin K2 in thyA(−) mutants), the skilled person would not have considered to commercialize e.g. a functional dairy food product made by use of herein described thyA(−) mutants for treatment and/or prevention of vitamin K deficiency in a mammal.

In the commercial market, e.g. a functional food product as described herein would have some kind of "label/announcement" informing the consumer of the high vitamin K content of the product (e.g. a yogurt or a cheese).

It is evident that the herein relevant amount of vitamin K2 in the composition relates to the amount of vitamin K2 derived from the presence of the thyA(−) mutant bacteria in the composition (e.g. a yogurt).

As shown in working example 1 herein—by fermenting milk by inoculating the milk with relevant amounts of the MBP71 thyA(−) mutant strain was obtained fermented milk with 26 μg/100 ml vitamin K2—i.e. 0.26 μg/ml vitamin K2.

If the composition is solid (i.e. not liquid as e.g. in a yogurt) the herein relevant amount of vitamin K2 may be measured as μg/g. An example of such a composition could e.g. be a dried composition of isolated thyA(−) mutant bacteria as such—such dried composition could e.g. be put into capsules and then e.g. sold as a medicament.

It is routine work for the skilled person to determine the amount of vitamin K2 in a composition of interest (e.g. yogurt or cheese) and it is also routine work to identify how much of the vitamin K2 that is derived from the presence of the thyA (−) mutant bacteria in the composition.

The skilled person can by use of well known assays (see e.g. Morishita T et al. 1999) routinely determine the amount of vitamin K2 in the composition as such (e.g. a yogurt).

Further, the skilled person can easily determine the amount of herein described thyA(−) mutant bacteria in the composition (e.g. $10^9$ cfu/ml).

Finally, the skilled person can routinely determine the average amount of vitamin K2 present on average in the individual bacteria of the composition and thereby routinely identify how much of the vitamin K2 that is derived from the presence of the thyA(−) mutant bacteria in the composition.

The scope/essence of the first aspect of the invention may alternatively be expressed as relating to a method for treatment and/or prevention of vitamin K deficiency in a mammal comprising administering a relevant amount of a composition to the mammal, wherein the composition is a composition comprising bacteria containing vitamin K2, wherein the amount of bacteria present in the composition results in:
   (a): at least 0.10 μg/(ml or g) of vitamin K2 in the composition; and wherein
   (i): the bacteria are thyA(−) mutants; and
   (ii): the bacteria are bacteria selected from the group consisting of the genera:
   *Lactococcus, Leuconostoc* and *Bacillus.*

Embodiments of the present invention are described below, by way of examples only.

DRAWINGS

FIG. 1: Overview of the nucleotide metabolism of *L. lactis*. Purine and pyrimidine metabolism is shown to the left and right of the FIGURE, respectively. Only the interconversions of the deoxyribonucleotide pyrimidines and precursors are shown in detail. Other reaction arrows may comprise more than one enzymatic reaction. All genes indicated have been localized in the genome of *L. lactis* IL1403, except ndk and dcd (Bolotin et. al 2001, Genome Res. 11:731-753). In the IL1403 genome sequence tdk is referred to as yfiG and tmk is referred to yeaB. Genes: deoB, phosphopentomutase; deoC, deoxyriboaldolase; pdp, thymidine phosphorylase; cdd, cytidine deaminase; tdk, thymidine kinase; dcdA, dCMP deaminase; thyA, TS; cmk, CMP kinase; dut, dUTPase; tmk, thymidylate kinase; ndk, NDP kinase; dcd, dCMP deaminase. PRPP, 5-phosphoribosyl-1-pyrophosphate.

DETAILED DESCRIPTION OF THE INVENTION

The Composition

As already discussed above, a herein commercially relevant composition is e.g. a fermented milk food product (such as a dairy food product) such as a yogurt or a cheese.

Due to the high vitamin K content of such a dairy product as described herein and the use of it for treatment and/or prevention of vitamin K deficiency—such a dairy product may be termed a functional food product.

Accordingly, in a preferred embodiment the composition of the first aspect is a food or feed product—preferably a food product.

Preferably, the food product is animal milk fermented with thyA(−) bacteria as described herein—e.g. preferably a dairy product.

Preferably, the animal milk is cow milk or goat milk.

Preferably, the dairy product is at least one dairy product selected from the list consisting of: milk, yogurt and cheese.

As discussed above, it may be advantageous to add a relatively large amount of LAB to the milk in order to obtain higher vitamin K production.

Accordingly, the animal fermented milk is preferably obtained by
(A): inoculating from $10^8$ to $10^{12}$ cfu/ml of thyA(−) bacteria as described herein to the animal milk; and
(B): fermenting the milk from 4 to 72 hours at a temperature from 10° C. to 50° C.

Alternatively, the composition comprises isolated thyA(−) mutant bacteria as described herein—preferably dried isolated thyA(−) mutant bacteria as described herein.

The term "isolated" should be understood as bacteria isolated after a suitable fermentation in a suitable medium—e.g. milk or a well known bacteria growth medium such a M17 medium.

As known to the skilled person—one may routinely isolate/harvest bacteria e.g. by centrifugation.

As discussed above, the vitamin K2 is constituents of the bacterial plasma membrane—i.e. vitamin K2 is present in the membrane of the LAB.

Accordingly, a composition comprising dried isolated thyA(−) mutant bacteria as described herein may e.g. be a medicament—e.g. it may be put into a pharmaceutically relevant capsule.

Bacteria Containing Vitamin K2

The term "bacteria"—in the first aspect described herein—is in plural since it makes no sense to here talk about a composition comprising only one single bacterium. However, it is evident that the composition may e.g. comprise $10^9$ cfu/ml bacteria of the same bacterial strain—e.g. MBP71 (DSM12891) as used in working examples herein.

Further, the composition may comprise other bacteria (e.g. wild-type thyA(+) bacteria) than herein described thyA(−) mutants.

The term "thyA(−) mutants" should be understood as the skilled person would understand it in the present context—i.e. as a mutant wherein the thyA gene is not active.

As known to the skilled person a gene may be inactivated in a number of well known ways—e.g. by a deletion, a mutation etc.

The thyA gene is a well known gene that has been sequenced and characterized in a number of different organisms—accordingly, the skilled person can routinely identify if a bacterium of interest is a thyA(−) mutant or not.

As discussed above, the bacteria of the first aspect as described herein are bacteria selected from the group consisting of: *Lactococcus*, *Leuconostoc* and *Bacillus*.

Preferably, the bacteria are bacteria selected from the group consisting of: *Lactococcus lactis*, *Leuconostoc lactis*, *Leuconostoc mesenteroides* and *Bacillus subtilis*.

More preferably, the bacteria are *Lactococcus lactis*.

Preferably, the *Lactococcus lactis* bacteria are *Lactococcus lactis* subsp. *lactis* or *Lactococcus lactis* subsp. *cremoris*.

More preferably, the bacteria are *Lactococcus lactis* subsp. *lactis*.

In a preferred embodiment, the bacteria are the thyA(−) *Lactococcus lactis* mutant strain MBP71 deposited under the accession number DSM12891.

As discussed above, DSM12891 is described in WO00/01799A2 (Chr. Hansen A/S) and was deposited before the PCT filing date of WO00/01799A2.

Amount of Vitamin K2 in the Composition

As discussed above, the composition as described herein is a composition, wherein the amount of bacteria present in the composition results in:
(a): at least 0.10 μg/(ml or g) of vitamin K2 in the composition.

As discussed above, it is routine work for the skilled person to determine the amount of vitamin K2 in a composition of interest (e.g. yogurt or cheese) and it is also routine work to identify how much of vitamin K2 is derived from the presence of the thyA(−) mutant bacteria in the composition.

The skilled person may use well known assays (see e.g. Morishita T et al. 1999) to determine this.

Preferably, there is at least 0.15 μg/(ml or g) of vitamin K2 in the composition, more preferably there is at least 0.20 μg/(ml or g) of vitamin K2 in the composition.

Sometimes it may be relevant to have a quite concentrated solid composition of e.g. freeze-dried dried composition of isolated thyA(−) mutant bacteria as such—accordingly, it may be preferred that the composition is a composition, wherein there in point (a) is at least 0.10 μg/mg of vitamin K2 in the composition.

In order to get such an amount of vitamin K2 in the composition—the composition as described herein normally comprises from $10^8$ to $10^{12}$ cfu/(ml or mg) of the bacteria of the first aspect.

The term cfu/(ml or mg) shall here be understood as essentially relating to the total number of cells present per ml or mg in the composition (e.g. a cheese).

In the case of dead cells, the number of cells is determined using a counting chamber, as is well known to the skilled person.

Use for Treatment and/or Prevention of Vitamin K Deficiency in a Mammal

As discussed above, before the knowledge of the present invention (i.e. high vitamin K2 in thyA(−) mutants), the skilled person would not have considered to commercialize e.g. a functional dairy food product made by use of herein described thyA(−) mutants for treatment and/or prevention of vitamin K deficiency in a mammal.

In the commercial market, e.g. a functional food product as described herein would have some kind of "label/announcement" informing the consumer of the high vitamin K content of the product (e.g. a yogurt or a cheese).

Commercially, the herein most relevant mammal is a human.

As known to the skilled person, the term "vitamin K deficiency" is a well known and defined pathological condition for the skilled person.

Below some common general knowledge in relation to vitamin K deficiency is described.

Vitamin K deficiency is a form of avitaminosis resulting from insufficient vitamin K. Vitamin K-deficiency may occur by disturbed intestinal uptake (such as would occur in a bile duct obstruction), by therapeutic or accidental intake of vitamin K antagonists or, very rarely, by nutritional vitamin K deficiency. As a result, Gla residues are inadequately formed and the Gla-proteins are insufficiently active.

Lack of control of the three processes mentioned above may lead to the four following: stomach pains; risk of massive uncontrolled bleeding; cartilage calcification; and severe malformation of developing bone or deposition of insoluble calcium salts in the walls of arteries. The deposition of calcium in soft tissues, including arterial walls, is quite common, especially in those suffering from atherosclerosis, suggesting that Vitamin K deficiency is more common than previously thought.

As discussed above vitamin K deficiency is well known to be associated with decreased bone health—e.g. malformation of developing bone or bone strength.

Accordingly, in a preferred embodiment the treatment and/or prevention of vitamin K deficiency is for improving bone health in a mammal.

The improvement of bone health may be related to less malformation of developing bone.

Alternatively, the treatment and/or prevention of vitamin K deficiency are for treatment and/or prevention of stomach pains; risk of uncontrolled bleeding or cartilage calcification.

Whether it is treatment or prevention of vitamin K deficiency will generally depend on the type of composition used (e.g. dairy product or a medicament).

In case it is a dairy product (e.g. a yogurt)—the e.g. yogurt may be sold to "healthy" people and it may therefore be seen as prevention of vitamin K deficiency (e.g. "normal" people obtain an improvement of their general bone health and therefore there is a prevention of bone problems).

In the case that the composition is a medicament, it may be more related to treatment of evidently sick people—e.g. a person with severe malformation of developing bone or a person with stomach pains.

In short, in the present context the skilled person will easily be able to identify the difference between treatment and prevention of vitamin K deficiency.

Commercially, the herein most relevant mammal is a human.

Alternatively, the mammal may e.g. be a cow, a pig, a goat, a dog, a cat or a rabbit.

The skilled person may—based on common knowledge—identify how much composition should preferably be administered to the mammal.

If the composition is e.g. a yogurt it will of course essentially be up to the consumer how much yogurt he/she wants to eat.

If the composition is a medicament, e.g. the physician will know how much e.g. the patient should have to get the treatment/prevention.

EXAMPLES

Example 1

*Lactococcus Lactis* thyA(−) Mutant MBP71 (DSM12891)—Increased Vitamin K2 Production The thyA(+) "wild-type"/mother strain for the *Lactococcus lactis* thyA(−) mutant MBP71 (DSM12891) is termed MBP68 herein.

The "wild-type"/mother strain *Lactococcus lactis* subsp. *lactis* MBP68 was grown under respiratory conditions (100 mL, M17+1% lactose, 5 ppm hemin, with vigorous agitation at 30° C.). OD600 of the stationary culture was 6.5 (average of triplicates). An amount of cells to yield OD 1.0 in 100 mL was removed and the cells were centrifuged down at 4° C. The cells were resuspended in 5 mL of cow milk with 3.5% fat ("whole milk"). These 5 mL were inoculated into 95 mL "whole milk" at 4° C. thus giving an inoculation level of OD=1.0. After ca. 20 h of incubation at 30° C. the sample was frozen at −20° C. and sent to analysis of vitamin K2.

The analysis of vitamin K2 was made by a process according to the art—i.e. an analytical procedure giving the same result as would be obtained by using the analytical procedure described in Morishita T et al. 1999. Production of Menaquinones by Lactic Acid Bacteria. J. Dairy. Sci. 82:1897-1903.

This strain MBP68 yielded a concentration of 9 µg/100 mL of vitamin K2.

In the same experiment we tested the strain MBP71 (CHCC11590, DSM12891).

This is a mutant of MBP68 which has been deleted in the thyA gene encoding thymidylate synthase—i.e. a thyA(−) mutant strain. Such a mutant cannot synthesize dTTP without addition of thymidine, and therefore cannot replicate their genome. We grew this strain as MBP68 but with 20 mg/L thymidine added to the M17 medium. The stationary OD was 5.5. After that it was treated as above. Note that milk is essentially devoid of thymidine.

Surprisingly, MBP71 produced 26 µg/100 mL of vitamin K2, i.e. about 3-fold higher than that of MBP68. Experiments similar to the above were carried out several times, each time giving several-fold higher vitamin K2 production for MBP71 than MBP68.

Conclusions:

The thyA(−) mutant strain MBP71 produced about 3-fold higher amount of vitamin K2 as compared to the corresponding thyA(+) wild-type strain MBP68.

Both strains were added to the milk at inoculation level of OD=1.0.

Such an inoculation level may be considered as adding a relatively large amount of LAB to the milk—i.e. as discussed above there was a limited growth (cell division) of the LAB in both experiments.

Accordingly, the fact that the thyA(−) mutant strain MBP71 cannot replicate its genome in the milk cannot be the only explanation for the SURPRISING result that the thyA(−) mutant strain produces significantly more vitamin K2.

Example 2

MBP71 thyA(−)—Different Fermentation Conditions

In one of these experiments MBP71 of Example 1 was inoculated into milk at OD 0.5 (rather than OD 1.0 as in Example 1). The vitamin K2 yield was in this case 17 µg/100 mL. An identical culture, but with 20 mg/L thymidine added to the milk, was also set up.

This culture yielded 15 µg/100 mL of vitamin K2, i.e. more or less the same as the culture without thymidine.

Conclusions:

This example shows that it is not directly the starvation for dTTP that results the increased vitamin K2, but rather the change in metabolism caused by the thyA gene inactivation.

Example 3

Test of Other Nucleotide Metabolism Mutants

To test it was not a general perturbation of nucleotide metabolism that gave increased vitamin K2 levels we also constructed a deletion mutant of purD (part of the purDEK operon), encoding phosphoribosylamine-glycine ligase, mutant of MBP68 in a similar manner as MBP71 (unpublished data).

Such a mutant cannot synthesize purine nucleotides de novo, neither ribo- nor deoxynucleotides, and requires an exogenous purine source for proliferation. This purD strain, CG75 (CHCC11704), was grown as MBP68 but with 100 mg/L of inosine added to the M17 medium, and treated as above. The stationary OD was 7.3. Note that milk is essentially devoid of purines.

The CG75 strain only produced 2 µg/100 mL of vitamin K2, i.e. several-fold less than MBP68.

Conclusions:

Overall, the results of Example 1 to 3 show that the mutant in thyA has a unique effect on vitamin K2 production.

Such a mutant is therefore a useful means of supplying more vitamin K2 in for example dairy products, thereby improving bone health for the general population.

REFERENCES

1. Morishita T et al. 1999. Production of Menaquinones by Lactic Acid Bacteria. J. Dairy. Sci. 82:1897-1903.
2. WO2008/040793A1 (Danone).
3. WO2008/040784A1 (Danone)
4. WO00/01799A2 (Chr. Hansen A/S)
5. Bolotin et. al 2001, Genome Res. 11:731-753
6. JP 2001 136959 A
7. JP 2000 080043 A
8. Tsukamoto et al; "Construction of a *Bacillus subtilis* (natto) with High Productivity of Vitamin K2 (Menaquinone-7) by Analog Resistance"; Bioscience Biotechnology Biochemistry; vol. 65(9), pages 2007-2015, 2001

The invention claimed is:

1. A method for treating vitamin K deficiency in a mammal in need thereof, comprising administering to the mammal a composition comprising an effective amount of bacteria that produce vitamin K2, wherein:
   (i) the bacteria are selected from the group consisting of the genera *Lactococcus, Leuconostoc* and *Bacillus* and are thyA(-) mutants that produce an increased amount of vitamin K2 in comparison to the wild-type bacteria of said genera; and
   (ii) the amount of bacteria present in the composition results in at least 0.10 µg/ml or 0.10 µg/g of vitamin K2 in the composition.

2. The method of claim 1, wherein the composition is a food product.

3. The method of claim 2, wherein the food product is at least one dairy product selected from the group consisting of milk, yogurt and cheese.

4. The method of claim 2, wherein the food product is animal milk fermented with the thyA(-) mutant bacteria.

5. The method of claim 4, wherein the animal fermented milk is obtained by
   (i) inoculating from $10^8$ to $10^{12}$ cfu/ml of the thyA(-) mutant bacteria to the animal milk and then
   (ii) fermenting the milk from 4 to 72 hours at a temperature from 10° C. to 50° C.

6. The method of claim 1, wherein the thyA(-) mutant bacteria are dried and isolated.

7. The method of claim 1, wherein the bacteria are *Lactococcus lactis*.

8. The method of claim 7, wherein the *Lactococcus lactis* bacteria are *Lactococcus lactis* subsp. *lactis* or *Lactococcus lactis* subsp. *cremoris*.

9. The method of claim 8, wherein the bacteria are the thyA(-) *Lactococcus lactis* subsp. *lactis* mutant strain MBP71 deposited under the accession number DSM12891.

10. The method of claim 1, wherein the composition comprises from $10^8$ to $10^{12}$ cfu/ml or from $10^8$ to $10^{12}$ cfu/mg of the thyA(-) mutant bacteria.

11. The method of claim 1, wherein the mammal is a human.

12. The method of claim 1, wherein the treatment of vitamin K deficiency improves bone health in a human.

13. The method of claim 12, wherein the improvement of bone health is less malformation of developing bone or bone strength.

14. The method of claim 1, wherein the amount of bacteria present in the composition results in at least 0.10 µg/mg of vitamin K2 in the composition.

* * * * *